United States Patent [19]

Barone

[11] Patent Number: 4,905,993
[45] Date of Patent: Mar. 6, 1990

[54] LUMBAR SUPPORT FOR WEIGHT LIFTING

[76] Inventor: Anthony J. Barone, 599 Porter Rd., RD #2, Howell, N.J. 07731

[21] Appl. No.: 336,912

[22] Filed: Apr. 12, 1989

Related U.S. Application Data

[63] Continuation-in-part of Ser. No. 167,048, Mar. 11, 1988, abandoned.

[51] Int. Cl.$^4$ ............................................ A63B 13/00
[52] U.S. Cl. .................................... 272/123; 128/78; 2/338
[58] Field of Search ........................ 272/123, 141, 143; 128/68, 69, 75, 78, 87 R, 87 B; 2/321, 322, 336, 338

[56] References Cited

U.S. PATENT DOCUMENTS

| | | | |
|---|---|---|---|
| 2,255,464 | 9/1941 | Hall, Jr. | 128/78 |
| 3,052,236 | 9/1962 | Schrieber | 128/78 |
| 3,888,481 | 6/1975 | Adams, Jr. et al. | 272/141 |
| 4,175,548 | 11/1979 | Henry | 128/78 X |
| 4,348,774 | 9/1982 | Woodson | 2/338 |
| 4,413,358 | 11/1983 | Jimenez | 2/321 |
| 4,545,370 | 10/1985 | Welsh | 128/78 |
| 4,597,386 | 7/1986 | Goldstein | 128/78 |
| 4,621,809 | 11/1986 | Pearl | 272/123 |
| 4,665,388 | 5/1987 | Ivie et al. | 272/123 X |
| 4,685,668 | 8/1987 | Newlin, Jr. | 272/123 |
| 4,689,833 | 9/1987 | Daniels | 2/322 |
| 4,698,854 | 10/1987 | Slimmon | 2/338 |
| 4,745,911 | 5/1988 | Bender | 272/123 X |
| 4,756,090 | 7/1988 | Pedrow | 128/78 X |
| 4,768,499 | 9/1988 | Kemp | 128/78 |
| 4,782,535 | 11/1988 | Yewer, Jr. et al. | 2/321 |
| 4,796,315 | 1/1989 | Crew | 128/78 X |
| 4,799,675 | 1/1989 | Helmer | 272/123 |
| 4,802,667 | 2/1989 | Aliner | 272/123 |

Primary Examiner—Richard J. Apley
Assistant Examiner—Robert W. Bahr
Attorney, Agent, or Firm—Charles I. Brodsky

[57] ABSTRACT

A miniature lumbar block is secured along an inside of the belt normally worn by power lifters so as to enhance the maintaining of the normal lordotic curve in the lower spine while lifting. The lumbar block incorporates an extension which contacts against the spinous process of a wearer in use, but is of a width to just fall short of contacting the paravertebral muscles when centered against the spinous process.

10 Claims, 3 Drawing Sheets

LUMBAR SUPPORT FOR WEIGHT LIFTING

This is a continuous-in-part of my application, Ser. No. 07/167,048, filed March 11, 1988, now abandoned.

FIELD OF THE INVENTION

This invention relates to power weight lifting and, more particularly, to a lumbar support at an inside of the belt normally worn by power lifters so as to enhance the maintaining of a normal lordotic curve in the lower spine while lifting.

BACKGROUND OF THE INVENTION

As is well known and understood, the arc of a normal lordotic curve in the lower spine is generally accepted to be of the order of 19 cm. As is also well known and understood, power weight lifters wear a leather belt tied around their waist while lifting, in an attempt to maintain this lordotic curvature in giving the optimum mechanical advantage to assist them in competition. Especially in "dead lifts" and in "squat lifts", the participant concentrates on positioning his, or her, legs and spine to give the greatest mechanical advantage during the lift itself. With such activities, the tendency of the lower spine is to straighten, and the use of the typical belt around the waist is tied sufficiently tightly in an attempt to maintain the lordotic curvature in providing the most mechanical advantage.

Experience has shown, however, that no matter how tightly the belt is kept—consistent with a degree of comfort—there still exists a tendency for the belt to "give", most noticeably when the lifter leans forward, and a degree of loss of the lordotic curve can thus result. Besides this resulting in a decrease in the biomechanical advantage available, such "give" has also been traced as a cause for the typical injuries of the lumbar postural muscles with result—namely, sprains and strains.

SUMMARY OF THE INVENTION

As will become clear hereinafter, the present invention incorporates a miniature lumbar block at an inside of the power lifter's belt, adjacent to the lifter's lower spine. In a preferred embodiment to be described, the lumbar block will be seen to be generally in the configuration of a half cylinder with an extension layered onto the curvilinear arc of the cylindrical surface. As will be seen, such extension is aligned to orient against the spinous process of the wearer, with the linear portion of the half-cylinder resting against the inside surface of the belt being worn. Any appropriate arrangement for securing the lumbar block to the inside of the belt is appropriate, either permanently (as an integral part of the manufacture or as by a sewing onto the belt thereafter), or temporarily (as by the use of frictional securements or of elastic strap securements which encircle the belt to be held in place thereby). In accordance with a preferred embodiment of the invention, the layered extension adjacent the spine is selected of a width so as to fill the indentations formed by the contraction of the erector spinal muscles during the lifting operation, and of a thickness both sufficient to fill in such indentations, but yet not enough so that the curvilinear section of the half-cylindrical portion contacts the paravertebral muscles when centered against the spinous process. As will be readily appreciated, both the spinal extension and the paraspinal block, comprising these structures, are formed of sufficiently rigid material to supply the support and mechanical advantage required, and to hold the spine automatically in place. As will be noted, a side-advantage of the embodiment to be described will also be seen to be an opportunity for the lifter to spend less time in concentrating on the positioning of the legs and spine before beginning the lift, as the lumbar support automatically sustains the lordotic curvature in the best position to optimize the mechanical advantage; thus, the mental energies can be devoted to a concentration on the mechanics of the lift process itself.

BRIEF DESCRIPTION OF THE DRAWINGS

These and other features of the invention will be more clearly understood from a consideration of the following description, taken in conjunction with the accompanying drawings, in which.

DETAILED DESCRIPTION OF THE DRAWINGS

Figure 1:
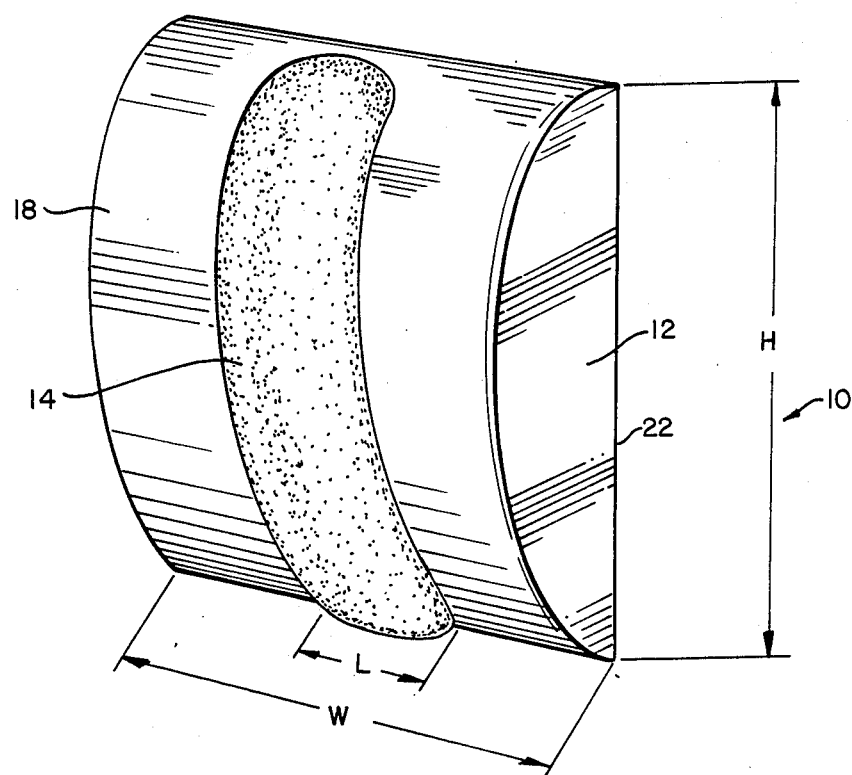
FIG. 1 is a front perspective view of a lumbar support constructed in accordance with a preferred embodiment of the invention.
Figure 2:
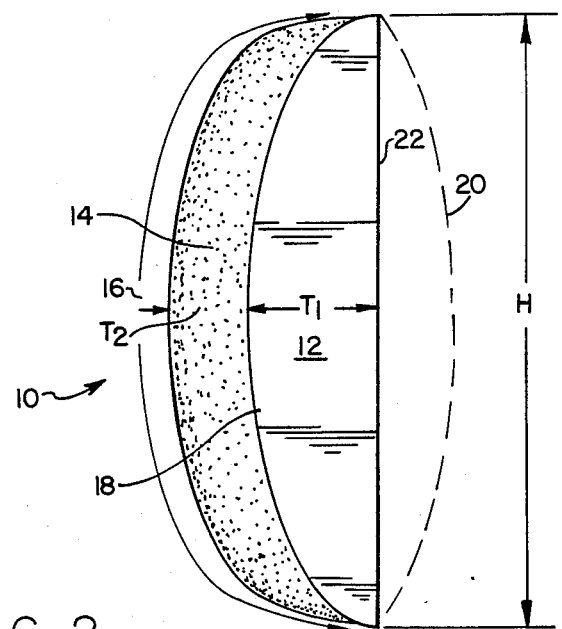
FIG. 2 is a side view of the lumbar support of FIG. 1.

Referring now to FIGS. 1 and 2, the lumbar support 10 is illustrated in the configuration of a half cylinder 12 having an extension 14 layered onto the curvilinear arc of the cylindrical surface 18. As will be understood, the half-cylinder 12 serves as the paraspinal block, while the extension 14 also serves as the spinal extension. Typically formed of a sufficiently rigid, resilient, pliant material to hold the spine automatically in place (e.g. leather over a high density foam), the paraspinal block 12 and spinal extension 14 will be understood to be a part of the weight lifting belt in any appropriate manner —as by being an integral part of its manufacture, or by being secured to it either temporarily or permanently, as by elastic straps, friction securements, sewing, etc. In such temporary securement arrangements, such holding devices —illustrated at 20, for example—encircle the belt whose abutting surface is in contact with the adjoining surface 22 of the paraspinal block 12.

In a preferred construction of the invention, the width W of the paraspinal block 12 was selected to be 15.3 cm, along with a height H ranging from 10.3 cm to 15.3 cm depending upon the height of the weight lifting belt employed. The thickness $T_1$ of the paraspinal block 12 was selected to be 1.0 cm and the thickness $T_2$ of the spinal extension 14 was selected to be 0.5 cm. The curvilinear arc 16 defined by the spinal extension 14 was selected at 19 cm, as representative of the lordotic curve measured between $L_5$ and $T_{12}$ on the spine. Additionally, the spinal extension 14 was positioned midway between the left and right sides of the paraspinal block 12, and oriented substantially orthogonal to the length of the belt with which the block 12 cooperates.

In using the lumbar support to be secured to the weight lifting belt, all that is required is to secure the support 10 to the belt and then arrange the belt so that the spinal extension 14 is centered against the spinous process and of sufficient width L to just fall short of contacting the paravertebral muscles—with the width L being typically about 2.5 cm. In using the weight lifting belt with the lumbar support as an integral part of its manufacture, all that is required is to arrange the support so that the spinous extension 14 contacts against the spinous process of the wearer. Experience has shown that with such width L, such a lumbar support 10 will increase the biomechanical advantage by maintaining the lordotic curve during the lifting process.

Figure 3:
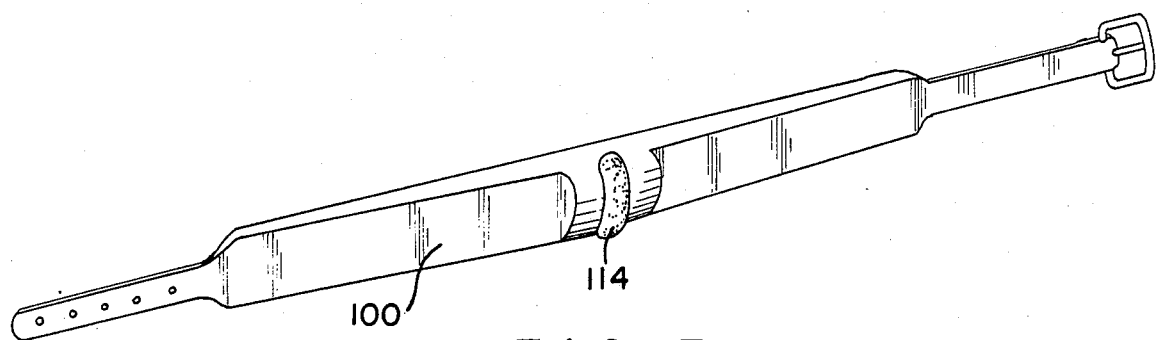
FIGS. 3–5 respectively show a front perspective view, a top view, and a partial sectional view of the lumbar support of FIG. 1 as it would be utilized in a weight lifting belt (with which it is integrally manufactured) according to the invention.
Figure 4:
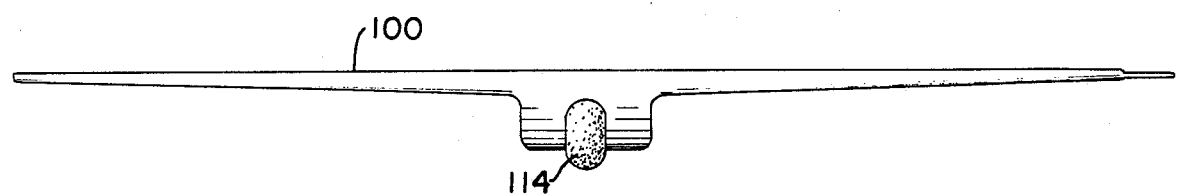
Figure 5:
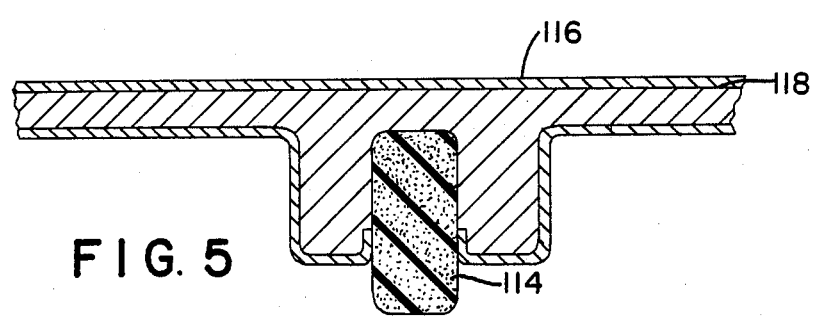

FIGS. 3–5 (not-to-scale) show various views of the lumbar support of FIGS. 1 and 2 as it could be utilized in a weight lifting belt with which it is integrally manufactured. The weight lifting belt is shown as 100, and could be composed of a leather, or leather-like, material, in housing the support and spinal extension, here shown as 114. As with the support of FIGS. 1 and 2, the width of the spinal extension 114 is selected of the order of 2.5 cm so that the spinal extension 114 fills the indentations formed by the contraction of the erector spinal muscles but does not extend to contact the paravertebral muscles. (Reference numeral 116 here represents the outside surface of the belt 100, and reference numeral 118 identifies a cushioning, or sponge-like inner material, oftentimes employed in the belt manufacture.)

Figure 6:
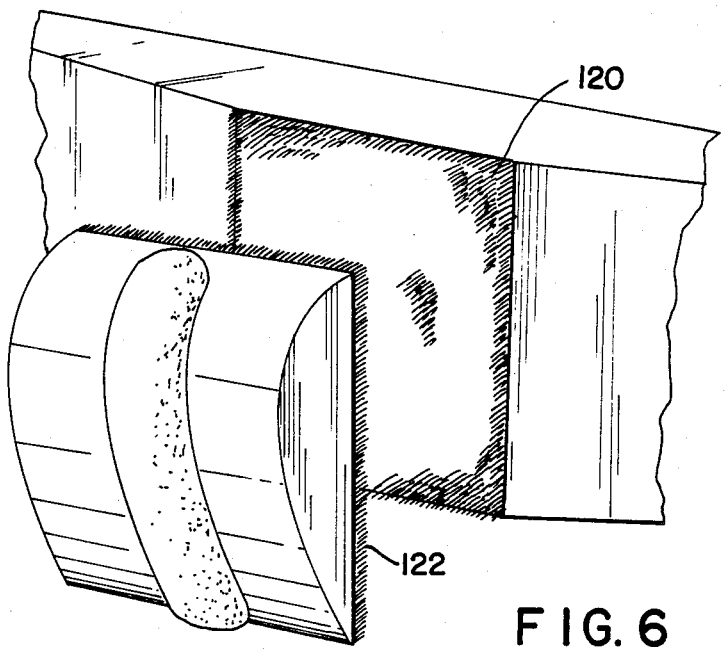
FIG. 6 shows one method of temporarily securing the lumbar support of FIG. 1 to the inside of a weight lifting belt in maintaining the lordotic curvature.

FIG. 6 illustrates one manner of temporarily securing the lumbar support of FIGS. 1 and 2 to a weight lifting belt with which it is not integrally manufactured. In this version, a pair of friction securement surfaces are utilized, one at the belt 120, and one at the lumbar support 122. As previously noted, the lumbar support could alternatively be secured to the belt by elastic encircling straps or by sewing.

Figure 7:
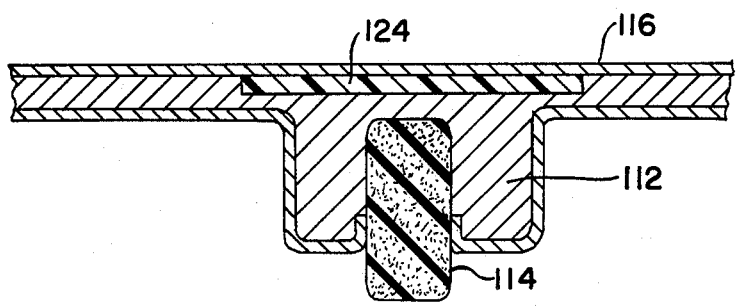
FIG. 7 shows a partial sectional view of a second lumbar support embodying the invention, incorporating a metal, or similar, support plate adjacent to the back of the weight lifting belt to further assist in the maintenance of the lordotic curve.

FIG. 7 shows a partial sectional view of a modification of the lumbar support of FIGS. 1 and 2, incorporating a metal, or similar, support plate 124 to further assist in maintaining the lordotic curve of the wearer. The plate 124 will be seen to be inserted within the belt 100, between the outside surface 116 and the paraspinal block 112, extending along the width W of the paraspinal block.

Figure 8:
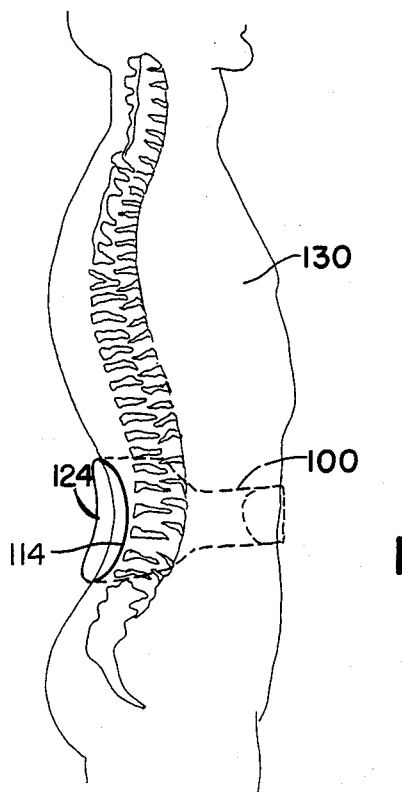
FIG. 8 is a sectional view showing the positioning of the lumbar support and weight lifting belt on the user.

FIG. 8 shows the positioning of the lumbar support and weight lifting belt when in use. When constructed in the manner described above, the spine will be more stabilized during the various weight lifting movements, by the support-belt combination, and the lordotic curve will be maintained to help increase mechanical advantage.

While there has been described what are considered to be preferred embodiments of the present invention, it will be readily appreciated that modifications can be made by those skilled in the art without departing from the scope of the teachings herein of providing a miniature lumbar block for enhancing the maintenance of the normal lordotic curve in the lower spine while weight lifting. Thus, for example, whereas specific materials have been suggested as available for use in forming the lumbar support of the invention, it will be appreciated that any type of pliable, resilient material may be employed in providing the support required. For at least such reason, therefore, resort should be had to the claims appended hereto for a correct understanding of the scope of the invention.

I claim:

1. Apparatus comprising:
 a weight lifting belt releasably placed around the waist of a user, said belt including
 (a) a support block in the configuration of a half cylinder having a curvilinear arc surface extending outwardly from a flat inner surface of said belt;
 (b) with said support block having an extension layered onto the curvilinear arc of the cylindrical surface of said half-cylinder;
 (c) with said extension being oriented substantially orthogonal to the length of said belt; and
 (d) with said extension being of a width of the order of 2.5 cm;
 such that when said weight lifting belt is worn with said extension centered about the spinous process of a user, said extension falls short of contacting the paravertebral muscles of said user;
 whereby the lordotic curve of the user can be maintained while performing weight lifting maneuvers.

2. The apparatus of claim 1 wherein said support block is substantially 15.3 cm in width.

3. The apparatus of claim 2 wherein said support block is of a height varying from 10.3 cm to 15.3 cm.

4. The apparatus of claim 3 wherein said support block is substantially 1.0 cm in thickness.

5. The apparatus of claim 4 wherein said extension is substantially 0.5 cm in thickness.

6. The apparatus of claim 5 wherein said extension is layered onto said cylindrical surface substantially 19 cm in length.

7. The apparatus of claim 6 wherein said support block is composed of a resilient, pliable material.

8. The apparatus of claim 6 wherein said weight lifting belt also incorporates a metal support plate on said inner surface from which said support block extends.

9. The apparatus of claim 6 wherein said support block is manufactured integrally with said weight lifting belt.

10. The apparatus of claim 6 wherein said support block is frictionally secured to said weight lifting belt.

* * * * *